(12) United States Patent
Anderson et al.

(10) Patent No.: US 6,613,085 B1
(45) Date of Patent: *Sep. 2, 2003

(54) PROSTHETIC HEART VALVE ROTATOR TOOL (75) Inventors: Kimberly A. Anderson, Eagan; William R. Holmberg, St. Paul, both of MN (US)

(73) Assignee: St. Jude Medical, Inc., St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/938,654

(22) Filed: Sep. 26, 1997

Related U.S. Application Data (63) Continuation-in-part of application No. 08/594,972, filed on Jan. 31, 1996, now Pat. No. 5,788,689.

(51) Int. Cl.[7] .................................................. A61F 2/24
(52) U.S. Cl. .......................... 623/2.11; 623/2.1; 606/1
(58) Field of Search ................ 606/1, 53, 72, 606/170, 180; 623/1.24, 1.26, 2.1, 2.11, 66.1, 902

(56) References Cited

U.S. PATENT DOCUMENTS

| 3,587,115 A | 6/1971 | Shiley |
| 3,628,535 A | 12/1971 | Ostrowsky et al. |
| 3,763,548 A | 10/1973 | Anderson |
| 3,800,403 A | 4/1974 | Anderson et al. |
| 3,839,741 A | 10/1974 | Haller |
| 3,959,827 A | 6/1976 | Kaster |
| 3,997,923 A | 12/1976 | Possis |
| 4,078,268 A | 3/1978 | Possis |
| 4,197,593 A | 4/1980 | Kaster et al. |
| RE30,507 E | 2/1981 | Kaster |
| 4,276,658 A | 7/1981 | Hanson et al. |
| 4,362,072 A | 12/1982 | Tillman |
| 4,453,434 A | 6/1984 | Lissy |
| 4,455,896 A | 6/1984 | Holmes |
| 4,510,825 A | 4/1985 | Neron et al. |
| 4,535,483 A | 8/1985 | Klawitter et al. |
| 4,599,081 A | 7/1986 | Cohen |
| 4,602,911 A | 7/1986 | Ahmadi et al. |
| 4,655,462 A | 4/1987 | Balsells |
| 4,680,031 A | 7/1987 | Alonso |
| 4,683,883 A | 8/1987 | Martin |
| 4,705,516 A | 11/1987 | Barone et al. |
| 4,790,843 A | 12/1988 | Carpentier et al. |
| 4,813,308 A | 3/1989 | Petrus |
| 4,826,144 A | 5/1989 | Balsells |
| 4,863,460 A | 9/1989 | Magladry |
| 4,892,017 A | 1/1990 | Kennedy et al. |
| 4,907,476 A | 3/1990 | Singleton |
| 4,915,366 A | 4/1990 | Balsells |
| 4,970,918 A | 11/1990 | Brewer et al. |
| 4,982,727 A | 1/1991 | Sato |
| 5,035,709 A | 7/1991 | Wieting et al. |
| 5,058,463 A | 10/1991 | Wannop |
| 5,071,431 A | 12/1991 | Sauter et al. |
| 5,104,406 A | 4/1992 | Curcio et al. |
| 5,178,633 A | 1/1993 | Peters |
| 5,197,980 A | 3/1993 | Gorshkov et al. |

(List continued on next page.)

Primary Examiner—Glenn K. Dawson
(74) Attorney, Agent, or Firm—Westman, Champlin & Kelly, P.A.; S. Koehler (57) ABSTRACT A prosthetic heart valve rotator tool includes an operator actuated member and a rotator engageable with a prosthetic heart valve for selectively rotating the prosthetic heart valve. An elongated bendable member has a first end secured to the operator actuated member and a second end secured to the rotator. The elongated bendable member transfers torque between the operator actuated member and the rotator. A covering member covers at least a portion of the elongated bendable member.

24 Claims, 5 Drawing Sheets

U.S. PATENT DOCUMENTS

| | | |
|---|---|---|
| 5,201,255 A | 4/1993 | Gegg |
| 5,354,330 A | 10/1994 | Hanson et al. |
| 5,403,305 A | 4/1995 | Sauter et al. |
| 5,476,510 A * | 12/1995 | Eberhardt et al. ............. 623/2 |
| 5,480,425 A | 1/1996 | Ogilive |
| 5,531,785 A * | 7/1996 | Love et al. .................... 606/1 |
| 5,582,607 A * | 12/1996 | Lackman ....................... 606/1 |
| 5,735,842 A * | 4/1998 | Krueger et al. ................ 623/2 |
| 5,788,689 A * | 8/1998 | Allan et al. .................... 623/2 |
| 5,800,531 A * | 9/1998 | Cosgrove et al. .............. 623/2 |
| 5,807,405 A * | 9/1998 | Vanney et al. ................. 623/2 |

* cited by examiner

PROSTHETIC HEART VALVE ROTATOR TOOL

CROSS REFERENCE TO RELATED APPLICATION

This application is a continuation-in-part of application Ser. No. 08/594,972, filed Jan. 31, 1996, now U.S. Pat. No. 5,788,689 which is incorporated herein by reference in its entirety.

FIELD OF THE INVENTION

The present invention relates to surgical instruments. More particularly, the present invention relates to a prosthetic heart valve rotator tool to orient a prosthetic heart valve into a preferred position during surgery.

BACKGROUND OF THE INVENTION

An implantable prosthetic heart valve is used as a replacement for an excised native heart valve of a patient. A typical prosthetic heart valve includes an annular valve orifice or body to provide a passageway for blood. At least one, and usually two, leaflets or occluders are mounted to an inner surface of the annular valve body and open or close with the flow of blood through the passageway.

A suture ring or sewing cuff is used to attach the heart valve to the patient's heart tissue. The sewing cuff is secured about the heart valve body and generally includes a biocompatible fabric that allows a needle and suture to pass through. The sewing cuff is placed proximate the tissue annulus at the site of the excised native heart valve. Sutures are passed through the tissue annulus and the sewing cuff, thereby securing the valve to the heart.

Prosthetic heart valves are implanted wholly or partially within the tissue annulus of the excised native valve. In some circumstances, a surgeon will want to position the prosthetic heart valve to optimize its location relative to the native structure. This is done as the sewing cuff is sutured to the heart tissue, or if the sewing cuff is rotatable relative to the valve, this can be done after the sewing cuff is secured to the heart tissue. Pending U.S. patent application 08/799,289, filed Feb. 13, 1997, entitled "ROTATABLE CUFF ASSEMBLY FOR A HEART VALVE PROSTHESIS" incorporated herein by reference, discloses a sewing cuff assembly having a resiliently deformed spring disposed along an annular seat of the valve body. The spring exerts a controlled force on the valve body, which results in a rotation-resisting torque when an outside force is applied to the valve. The rotation-resisting torque is sufficient to resist rotation during normal operation of the valve after implantation but low enough to permit the surgeon to rotate the valve during implantation.

However, in some instances, rotation of the prosthetic heart valve may be encumbered by lack of available space in which the surgeon has to work, especially in the case of small patients, for example, children. The lack of space is particularly prevalent when a prosthetic heart valve will be sutured in the mitral valve position.

Figure 5:
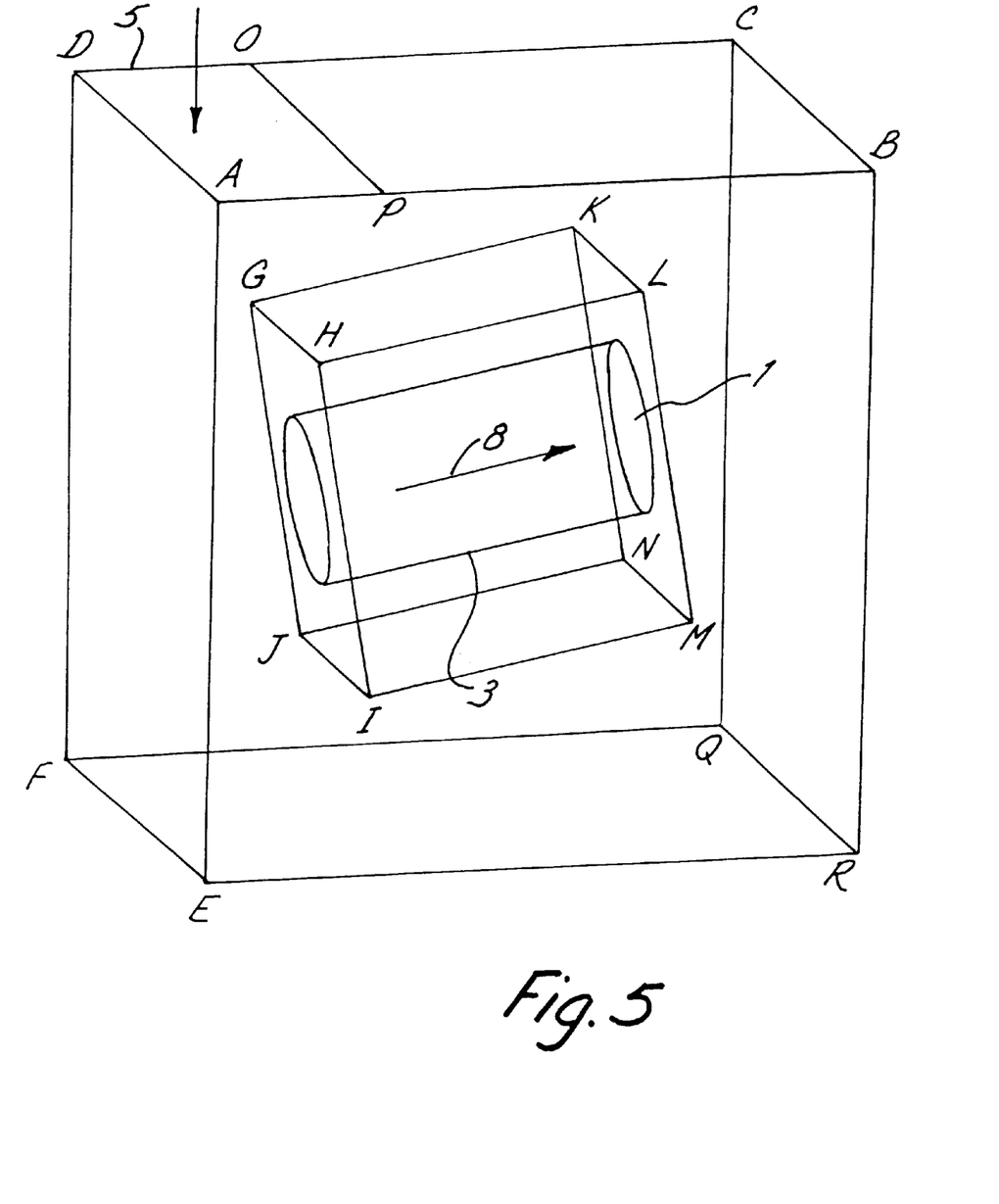
FIG. 5 is a schematic diagram representing a three dimensional view of a mitral valve in a patient's chest.

FIG. 5 is a schematic diagram generally illustrating the difficulties involved with orienting a prosthetic mitral valve 1 during surgery. In FIG. 5, a patient's open chest is represented by plane ABCD. The patient is lying on an operating table represented by plane EFQR. A surgeon faces the patient and is generally parallel to plane ADFE. Although the chest is open, the surgeon only has access to the prosthetic mitral valve 1 (generally lying in a plane KLMN) through a small access aperture 2 bounded by line segments ADOP. The access aperture 2 opens to a small cavity proximate a plane GHIJ, which represents access to the patient's atrium 3. In FIG. 5, line segment ER extends perpendicular through the patient's sternum, while planes ADFE and BCQR represent the patient's right and left lung, respectively. To successfully rotate the prosthetic mitral valve 1, the surgeon must break the plane GHIJ and engage the prosthetic mitral valve 1 at plane KLMN through the atrium 3 with sufficient thrust or force represented by arrow 8 and maintain this force in order to rotate the prosthetic mitral valve 1. Since the prosthetic mitral valve 1 is located in the plane KLMN which is not directly accessible from the patient's open chest and, in fact, is disposed downwardly toward the operating table at an acute angle, rotation of the prosthetic mitral valve 1 is difficult. To clarify the limited space with which the surgeon must work with, for an average man, the opening 2 may be only five inches long (line segment AD) and one and one-half inches wide (line segment AP). Access to the atrium 3 in plane GHIJ is approximately two and one-half to three inches from the opening 2 and approximately one and one-half inches from the right lung (plane ADEF). The atrium 3 is approximately one and one-half inches long. Of course, each of the foregoing dimensions is less for a smaller patient such as a child.

U.S. Pat. No. 5,403,305 discloses a prosthetic heart valve rotating device. The device includes an eccentric socket attached to a bendable shaft. The eccentric socket receives a rotator head. A spring retains the rotator head in the socket. Since an axis of the socket and rotator head is offset from the bendable shaft, rotation of the prosthetic heart valve requires rotation of the shaft about the axis of the rotator head.

SUMMARY OF THE INVENTION

A prosthetic heart valve rotator tool includes an operator actuated member and a rotator engageable with a prosthetic heart valve for selectively rotating the prosthetic heart valve. An elongated bendable member has a first end secured to the operator actuated member and a second end secured to the rotator. The elongated bendable member transfers torque between the operator actuated member and the rotator. A covering member covers at least a portion of the elongated bendable member.

DETAILED DESCRIPTION OF THE PREFERRED EMBODIMENTS

Figure 1:
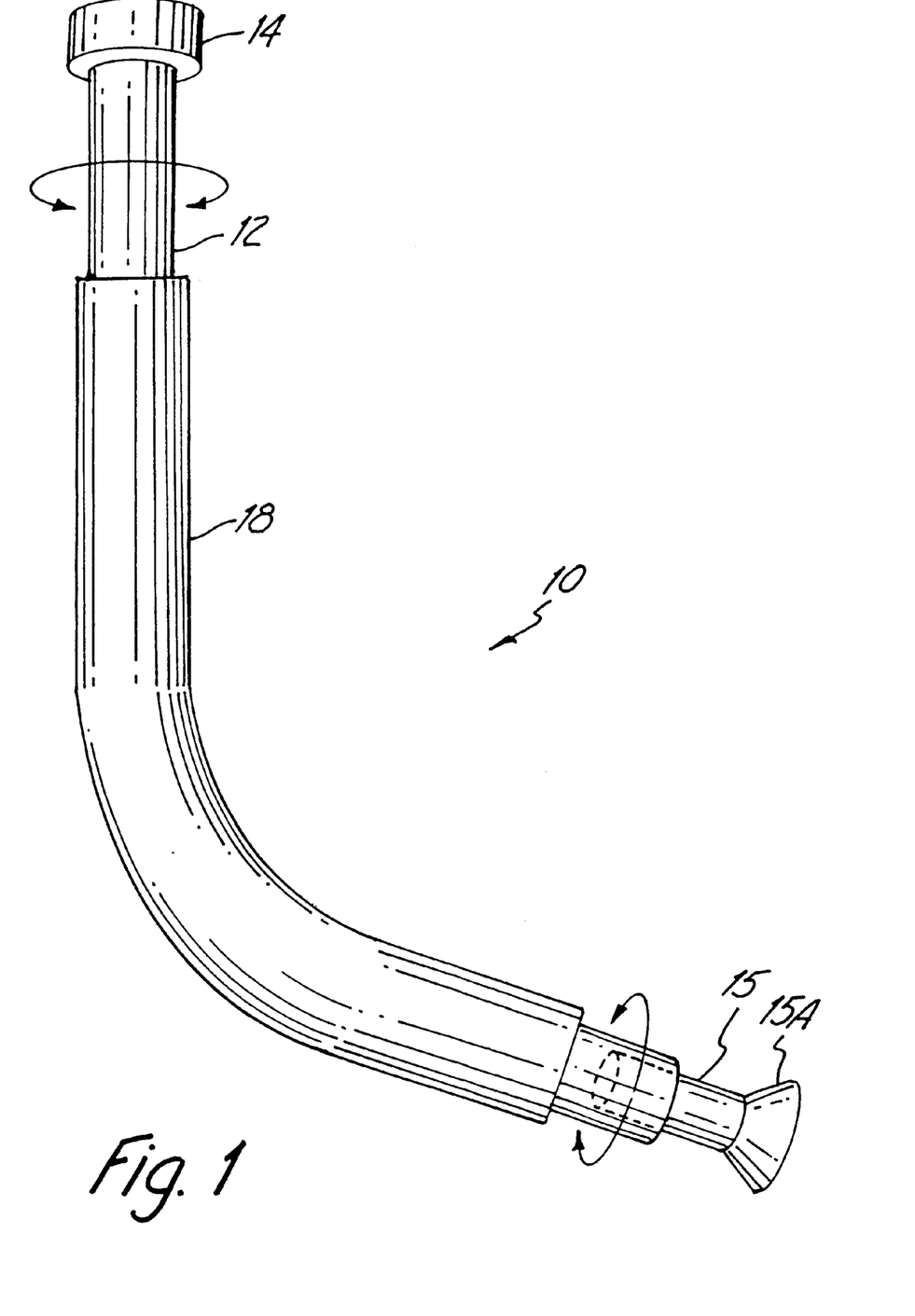
FIG. 1 is a perspective view of a first embodiment of a prosthetic heart valve rotator tool.

FIG. 1 illustrates a first embodiment of a prosthetic heart valve rotator tool 10 of the present invention. The prosthetic heart valve rotator tool 10 includes a flexible elongated shaft 12 extending from an operator actuated member or knob 14 to a rotator 15. The flexible shaft 12 extends through a flexible guide tube 18. The knob 14 is used to rotate the shaft 12 and is secured to or formed with the flexible shaft 12 on one end, while the rotator 15 is secured to the other end. This prevents the tube 18 from sliding off either end. Removal of either the knob 14 or the rotator 15 allows removal of the flexible shaft 12 from the tube 18 to facilitate cleaning and sterilization. The shaft 12, the knob 14, the rotator 15 and the tube 18 can all be made from a suitable material such as plastic, metal or a combination thereof. In this manner, the prosthetic heart valve rotator tool 10 can be made to be reusable or disposable, as desired. For instance, the shaft 12 and/or the tube 18 can be formed as a coiled or helical wire. In other embodiments, the shaft 12 can be made from a flexible material such as stainless steel, while the tube 18 can be made from a shape memory material such as Nitinol® (Nickel-titanium). This allows the shaft 12 or the tube 18 to be shaped from a first configuration to a second configuration. The shaft 12 or the tube 18 substantially maintain the second configuration after removal of the shaping force which allows the surgeon to hold the prosthetic heart valve rotator tool 10 with one hand while maintaining the rotator 15 in a desired position. The flexible shaft 12 and the tube 18 allow the prosthetic heart valve rotator tool 10 to be configured into an infinite array of positions. In addition, the shaft 12 or tube 18 can return to the first configuration after sterilization for re-use.

Throughout the Figures and embodiments of the present invention, the rotator 15 is generally depicted. Those skilled in the art will recognize that the rotator 15 includes a head 15A having a shape suitable for engagement with either prosthetic aortic valves or prosthetic mitral valves. Since prosthetic heart valves in general can be constructed with a single leaflet (occluder) or with multiple leaflets (occluders), an outer surface of the rotator head 15A is shaped in a known manner to properly engage the specific prosthetic valve used during surgery. Since the rotator head 15A can be formed in any one of a number of shapes, throughout the Figures, the enlarged head 15A will generally represent these engaging surfaces.

Figure 2:
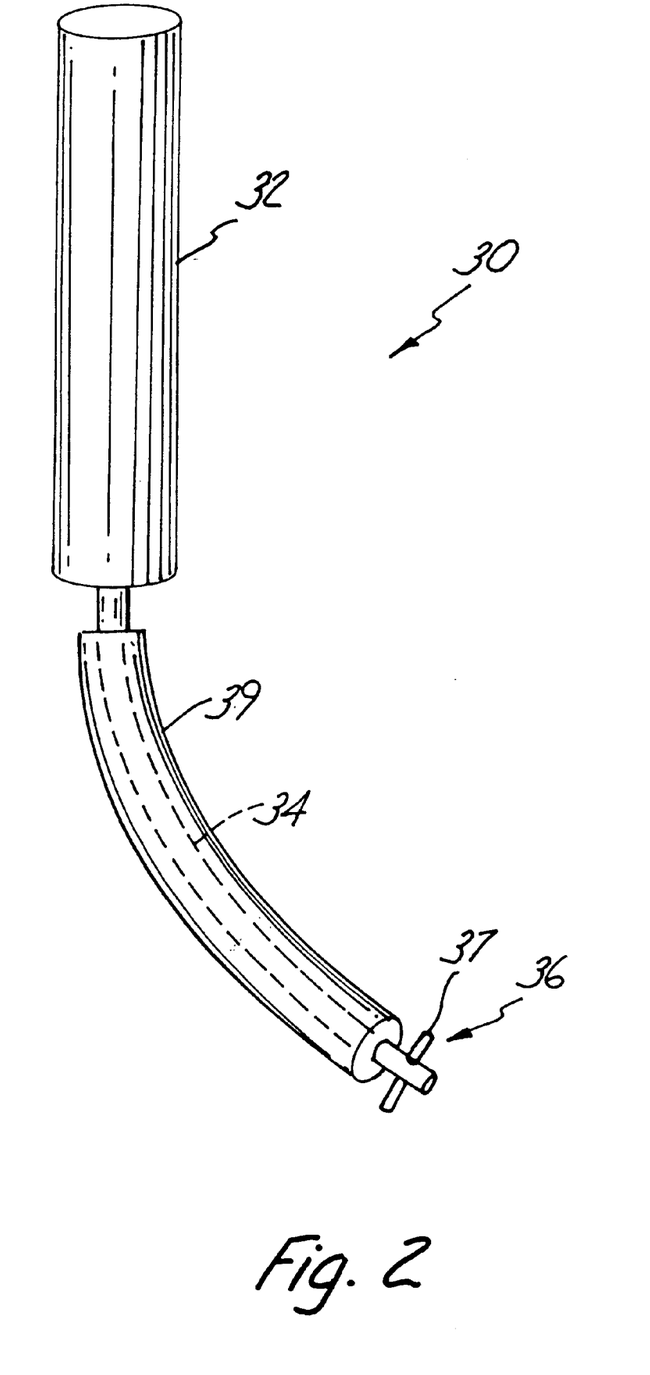
FIG. 2 is a perspective view of a second embodiment of a prosthetic heart valve rotator tool.

FIG. 2 illustrates a second embodiment of a prosthetic heart valve rotator tool 30 of the present invention. The prosthetic heart valve rotator tool 30 includes an elongated handle 32 joined to a flexible shaft 34. The shaft 34 includes an end 36 that is coupleable to the rotator 15. End 36 includes a pin 37 extending substantially normal to the shaft 34. The pin 37 is received by a suitable aperture, not shown, formed in the end of the rotator 15. The pin 37 helps transfer torque from the shaft 34 to the rotator 15. An outer tube 39 surrounds a portion of the shaft 34 between the handle 32 and the pin 37, allowing the shaft 34 to rotate therein. The outer tube 38 is made from flexible material like tube 18 so that it can be grasped and bent by a surgeon to properly position the rotator 15.

Figure 3:
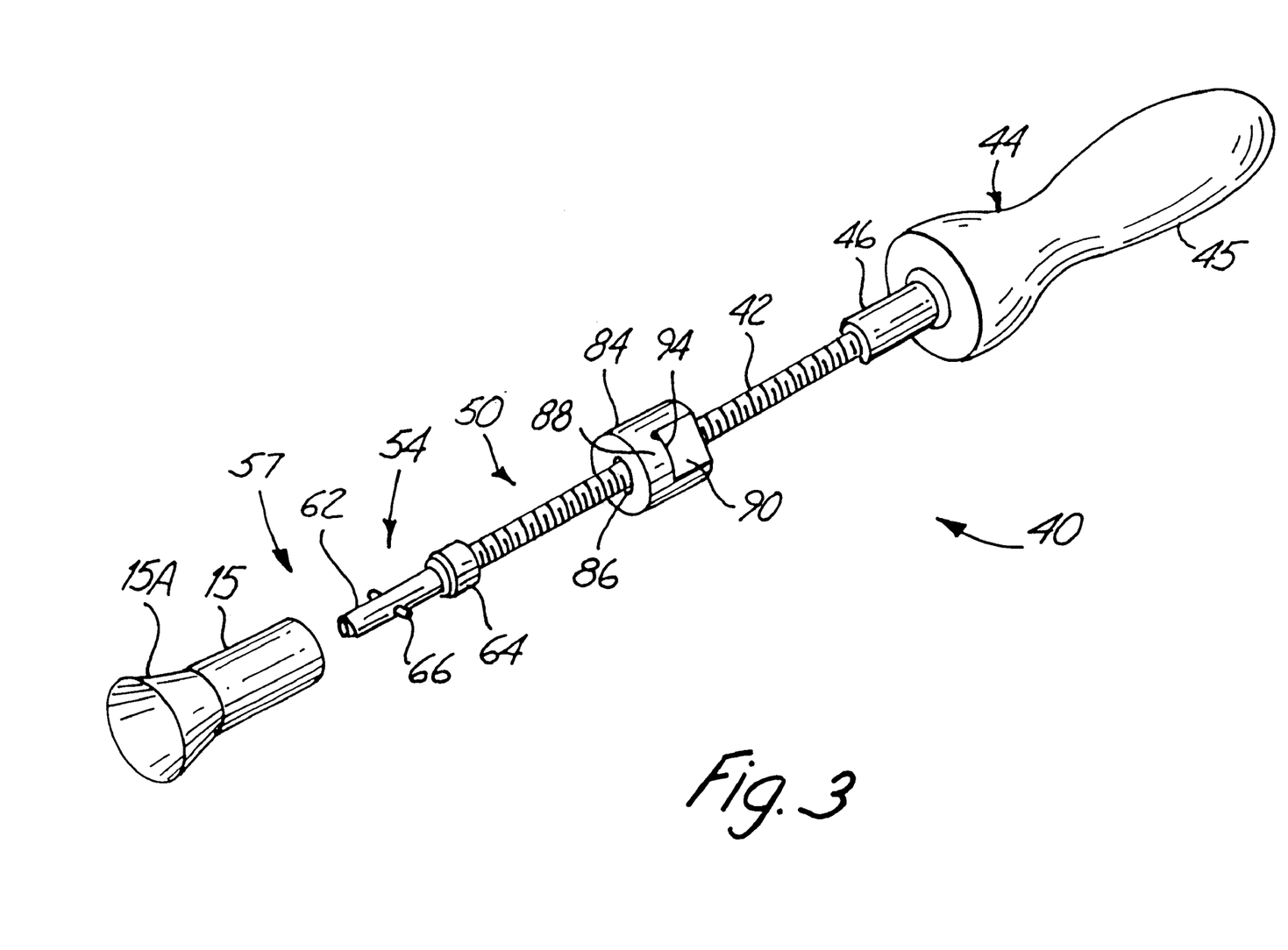
FIG. 3 is a perspective view of a third embodiment of a prosthetic heart valve rotator tool.
Figure 4:
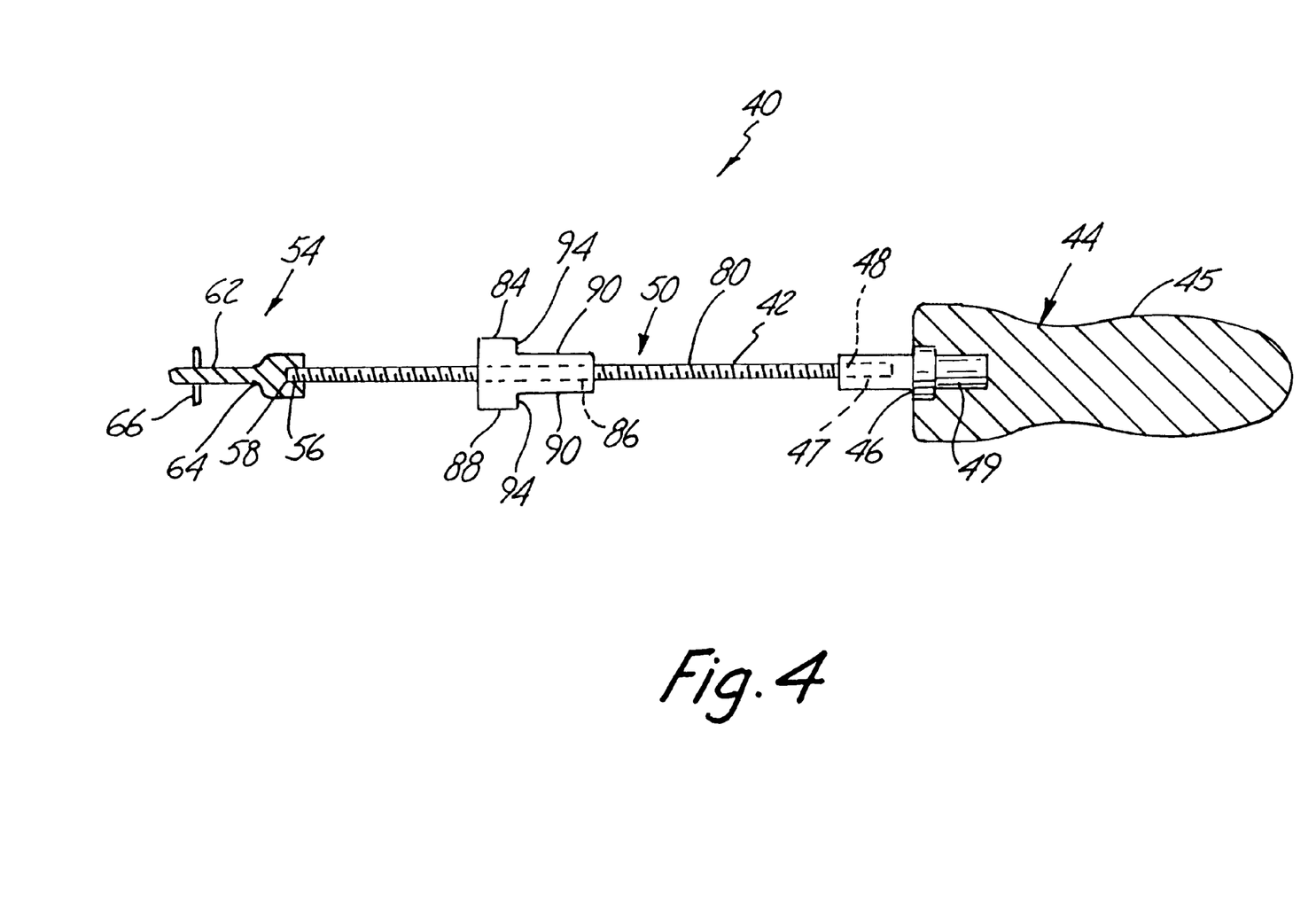
FIG. 4 is a sectional view of the third embodiment.

FIGS. 3 and 4 illustrate a third embodiment of a prosthetic heart valve rotator tool 40 of the present invention. The prosthetic heart valve rotator tool 40 includes a flexible elongated shaft 42 extending from a knob 44 to the rotator 15. In the embodiment illustrated, the knob 44 includes a core 46 having a recess 48 that receives a first end 47 of the flexible shaft 42. The core 46 is crimped or swagged onto the end of the flexible shaft 42. A handle 45 is secured to end 49 of the core 46. The handle 45 can be made from a sterilizable material such as plastic or metal, for example, a silicone or a thermoplastic elastomer such as Santoprene®.

In the embodiment illustrated, the flexible shaft 42 comprises a coiled wire assembly 50. The coiled wire assembly 50 forms a tube and can be made from a single strand or a plurality of strands, for example, seven strands made from a stainless steel wire. The coiled wire assembly 50 can be oriented in any necessary position so that the surgeon can easily grasp the knob 44, while having the rotator 15 engage the heart valve. The coiled wire assembly 50 transmits torque from the knob 44 to the rotator 15 allowing the rotator 15 to rotate about a stationary axis, while the knob 44 rotates about a second axis that can be oriented in a convenient position for the surgeon that is neither parallel nor aligned with the axis of the rotator 15.

In a preferred embodiment, the rotator 15 is detachable from a tip 54 formed on a second end 56 of the flexible shaft 42, where the rotator 15 and the tip 54 form a detachable coupling 57 with the axis of rotation of the coupling 57, the axis of rotation of the second and 56, the tip 54 and the axis of the rotator 15 all aligned. The tip 54 includes an inner recess 58 that receives the end 56 of the flexible shaft 42. In the embodiment illustrated, the tip 54 is crimped or swagged onto the end 56 of the flexible shaft 42. The tip 54 is made from a suitable material such as stainless steel or plastic such as Radel® (polyphenylsulfone) that can be sterilized.

The tip 54 includes a cylindrical rod portion 62 insertable into the rotator 15 and an enlarged annular flange 64. Although illustrated with the annular flange 64 larger than rod portion 62, the annular flange 64 can have a diameter equal to or less than the diameter of the rod portion 62. A pin 66 extends substantially normal to a longitudinal axis if the rod portion 62. The pin 66 is received by a suitable aperture, not shown, formed in the end of the rotator 15. The pin 66 can be formed with the shaft tip 54 or shaft 42. The pin 66 helps transfer torque from the knob 44 to the rotator 15 and helps keep the rotator 15 on the tip 54. When the rotator 15 is not attached to the tip 54, the rotator 15 can be used to hold the prosthetic heart valve in a suitable package during shipping, If desired, the tip 54 can be eliminated and the rotator 15 can be fixed to or formed with the flexible shaft 42, thereby making coupling 57 non-detachable.

In one embodiment, an outer covering or sheath 80 covers the coiled wire assembly 50 from the rotator 15 or tip 54 to the knob 44. The covering 80 forms a protective layer over the coiled wire assembly 50 that prevents contaminants from being retained by individual turns of the coiled wire assembly 50. The covering 80 also allows the prosthetic heart valve rotator tool 40 to be easily sterilized and reused. The covering 80 is flexible and can be made from a suitable material such as silicone. The core 46 and tip 54 can be crimped over the outer covering 80.

In a further embodiment, a positioning collar 84 can be coupled to the flexible shaft 42, allowing the flexible shaft 42 to be rotated relative to the positioning collar 84. Preferably, the positioning collar 84 is also slidable along the flexible shaft 42 for at least a limited distance. In the embodiment illustrated, the positioning collar 84 includes a central bore 86 through which the flexible shaft 42 extends. The positioning collar 84 can be slid to any longitudinal position between the tip 54 and the knob 44. The positioning collar 84 can be made from a suitable material such as plastic, metal or a combination thereof and includes an outer surface 88 with recesses 90 for grasping. Flanges 94 help prevent the grasping device (e.g. fingers, forceps or the like) from slipping off the positioning collar 84. By holding the positioning collar 84, the surgeon can move the knob 44 relative to the rotator 15 to bend the flexible shaft 42 into a non-linear shape. The surgeon can then rotate the knob 44 in order to transmit torque through the flexible shaft 42 to the rotator 15 to rotate the prosthetic heart valve into the correct orientation.

The prosthetic heart valve rotator tool as set forth herein allows a surgeon to positively engage and rotate a heart valve to a desired position. The flexible shaft is secured to both the knob and the rotator in order to efficiently transfer torque to rotate the heart valve easily and safely in a surgical environment where access can be difficult. The flexible shaft is bendable allowing the rotator to be placed in any necessary position relative to the knob in order to engage the prosthetic heart valve. If desired, the flexible shaft can be made from a pliable material allowing the flexible shaft to be shaped from a first configuration to a second configuration, where the flexible shaft substantially maintains the second configuration after removal of the shaping force. This allows the flexible shaft to extend around corners or through difficult access areas within the body. The prosthetic heart valve rotator tool can be made at low cost since the various elements are readily available or are easy to manufacture using standard manufacturing methods such as injection molding. The embodiments described above provide a prosthetic heart valve rotator tool that can be made disposable or made from parts that can be conveniently separated for cleaning, sterilization and reassembly. When configured with a tip, the prosthetic heart valve rotator tool can be used with holders used in packaging prosthetic heart valves.

Although the present invention has been described with reference to preferred embodiments, workers skilled in the art will recognize that changes may be made in form and detail without departing from the spirit and scope of the invention. For instance, those skilled in the art will recognize that the bendable shaft can be made, for example, from a coiled wire, or a solid or hollow shaft.

What is claimed is:

1. A prosthetic heart valve rotator tool comprising:
   a rotator adapted to engage a prosthetic heart valve and selectively rotate the prosthetic heart valve;
   an elongated bendable member having a first end and a second end secured to the rotator, wherein the elongated bendable member is rotatable over a length of the elongated bendable member from the first end to the rotator with rotation of the first end to transfer torque to the rotator when an axis of rotation of the first end is not aligned with an axis of rotation of the rotator; and
   a collar coupled to the elongated bendable member, the collar being rotatable about the elongated bendable member and slidable along the elongated bendable member to and from a position proximate the second end at least a distance of approximately one-half an axial length of the collar and independent of a position of the collar along the elongated bendable member.

2. The prosthetic heart valve rotator tool of claim 1 wherein the collar includes opposed planar surfaces adapted to be held by a surgeon.

3. The prosthetic heart valve rotator tool of claim 1 wherein the elongated bendable member comprises a coiled wire assembly.

4. The prosthetic heart valve rotator tool of claim 3 wherein the coiled wire assembly comprises a plurality of strands.

5. The prosthetic heart valve rotator tool of claim 3 and further comprising a covering member covering the coiled wire assembly and being rotatable with the coiled wire assembly, wherein the collar is rotatable and longitudinally slidable over the covering member.

6. The prosthetic heart valve rotator tool of claim 1 wherein the elongated bendable member is made from a pliable material allowing the elongated bendable member to be shaped from a first configuration to a second configuration, the elongated bendable member substantially maintaining the second configuration after removal of a shaping force.

7. The prosthetic heart valve rotator tool of claim 6 wherein the elongated bendable member comprises a substantially solid shaft.

8. The prosthetic heart valve rotator tool of claim 1 wherein the elongated bendable member includes a tip at the second end, and wherein the rotator engages the tip and is removable from the tip.

9. The prosthetic heart valve rotator tool of claim 8 and further comprising a pin extending from the tip to transfer torque to the rotator.

10. The prosthetic heart valve rotator tool of claim 1 and further comprising an operator actuated member secured to the first end.

11. The prosthetic heart valve rotator of claim 10 wherein the operator actuated member, the rotator, the elongated bendable member and the collar are adapted for sterilization.

12. A prosthetic heart valve rotator tool comprising:
    rotator adapted to engage a prosthetic heart valve and selectively rotate the prosthetic heart valve;
    an elongated bendable member having a first end and a second end secured to the rotator, wherein the elongated bendable member is rotatable over a length of the elongated bendable member from the first end to the rotator with rotation of the first end to transfer torque to the rotator when an axis of rotation of the first end is not aligned with an axis of rotation of the rotator; and
    a bendable tube covering a portion of the elongated bendable member, the tube being rotatable about the elongated bendable member and slidable along the elongated bendable member independent of a position of the tube along the elongated bendable member.

13. The prosthetic heart valve rotator tool of claim 12 wherein the elongated bendable member comprises a substantially solid shaft.

14. The prosthetic heart valve rotator tool of claim 12 wherein the elongated bendable member includes a tip at the second end, and wherein the rotator engages the tip and is removable from the tip.

15. The prosthetic heart valve rotator tool of claim 12 and further comprising an operator actuated member secured to the first end.

16. A prosthetic heart valve rotator tool comprising:
    a rotator adapted to engage a prosthetic heart valve and selectively rotate the prosthetic heart valve; and
    an elongated bendable member having a first end and a second end, the second end having an axis of rotation, the rotator being secured to the second end with a coupling having an axis, the coupling consisting of a direct connection between the second end and the rotator such that an axis of rotation of the rotator is aligned with the axis of the coupling and the axis of rotation of the second end and wherein the elongated bendable member is rotatable over a length of the elongated bendable member to transfer torque from the first end to the rotator when an axis of rotation of the first end is not aligned with the axis of rotation of the rotator.

17. The prosthetic heart valve rotator tool of claim 16 wherein the elongated bendable member comprises a wire assembly having a plurality of strands.

18. The prosthetic heart valve rotator tool of claim 17 and further comprising a covering member over the wire assembly from proximate the first end to proximate the second end.

19. The prosthetic heart valve rotator tool of claim 18 wherein the covering member is rotatable with the wire assembly.

20. The prosthetic heart valve rotator tool of claim 17 and further comprising a tubular member enclosing a plurality of turns of the wire assembly.

21. The prosthetic heart valve rotator tool of claim 16 and further comprising an operator actuated member secured to the first end.

22. The prosthetic heart valve rotator tool of claim 16 and further comprising a collar rotatable about and slidable along the elongated bendable member.

23. The prosthetic heart valve rotator tool of claim 12 wherein the tube is made from a pliable material allowing the tube to be shaped from a first configuration to a second configuration, the tube substantially maintaining the second configuration after removal of a shaping force.

24. A prosthetic heart valve rotator tool comprising:
- a rotator adapted to engage a prosthetic heart valve and selectively rotate the prosthetic heart valve;
- an elongated bendable member having a first end and a second end secured to the rotator, wherein the elongated bendable member is rotatable over a length of the elongated bendable member from the first end to the rotator with rotation of the first end to transfer torque to the rotator when an axis of rotation of the first end is not aligned with an axis of rotation of the rotator; and
- a collar coupled to the elongated bendable member, the collar being rotatable about the elongated bendable member and slidable along the elongated bendable member independent of a position of the collar along the elongated bendable member within a limited extent from a first position proximate the first end to a second position proximate the second end.

* * * * *